United States Patent
Steiner et al.

(10) Patent No.: US 6,890,354 B2
(45) Date of Patent: *May 10, 2005

(54) BONE-TENDON-BONE ASSEMBLY WITH ALLOGRAFT BONE BLOCK AND METHOD FOR INSERTING SAME

(75) Inventors: Anton J. Steiner, Wharton, NJ (US); Arthur A. Gertzman, Stony Point, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 262 days.

This patent is subject to a terminal disclaimer.

(21) Appl. No.: 10/092,537

(22) Filed: Mar. 8, 2002

(65) Prior Publication Data

US 2003/0171811 A1 Sep. 11, 2003

(51) Int. Cl.$^7$ .................................................. A61F 2/08
(52) U.S. Cl. .................................. 623/13.14; 623/13.12
(58) Field of Search ........................... 623/13.11–13.2, 623/17.11, 17.16, 20.14–20.17

(56) References Cited

U.S. PATENT DOCUMENTS 5,609,636 A * 3/1997 Kohrs et al. .............. 623/17.16

OTHER PUBLICATIONS

U.S. Appl. No. 10/277,838.*

* cited by examiner

Primary Examiner—Corrine McDermott
Assistant Examiner—Hieu Phan
(74) Attorney, Agent, or Firm—John S. Hale; Gipple & Hale

(57) ABSTRACT

The invention is directed toward a bone block, a bone-tendon-bone assembly and method of tendon reconstruction in which at least one tendon replacement is extended between two bone blocks and fixed within each of two bone tunnels in the bones of a joint using interference screws. Each bone block has a central through going bore and at least one substantially parallel channel longitudinally cut in the exterior of the bone block body in which the ligament replacements are seated. One end of each bone block has a rounded recess leading from the central bore to the exterior parallel channel.

24 Claims, 6 Drawing Sheets

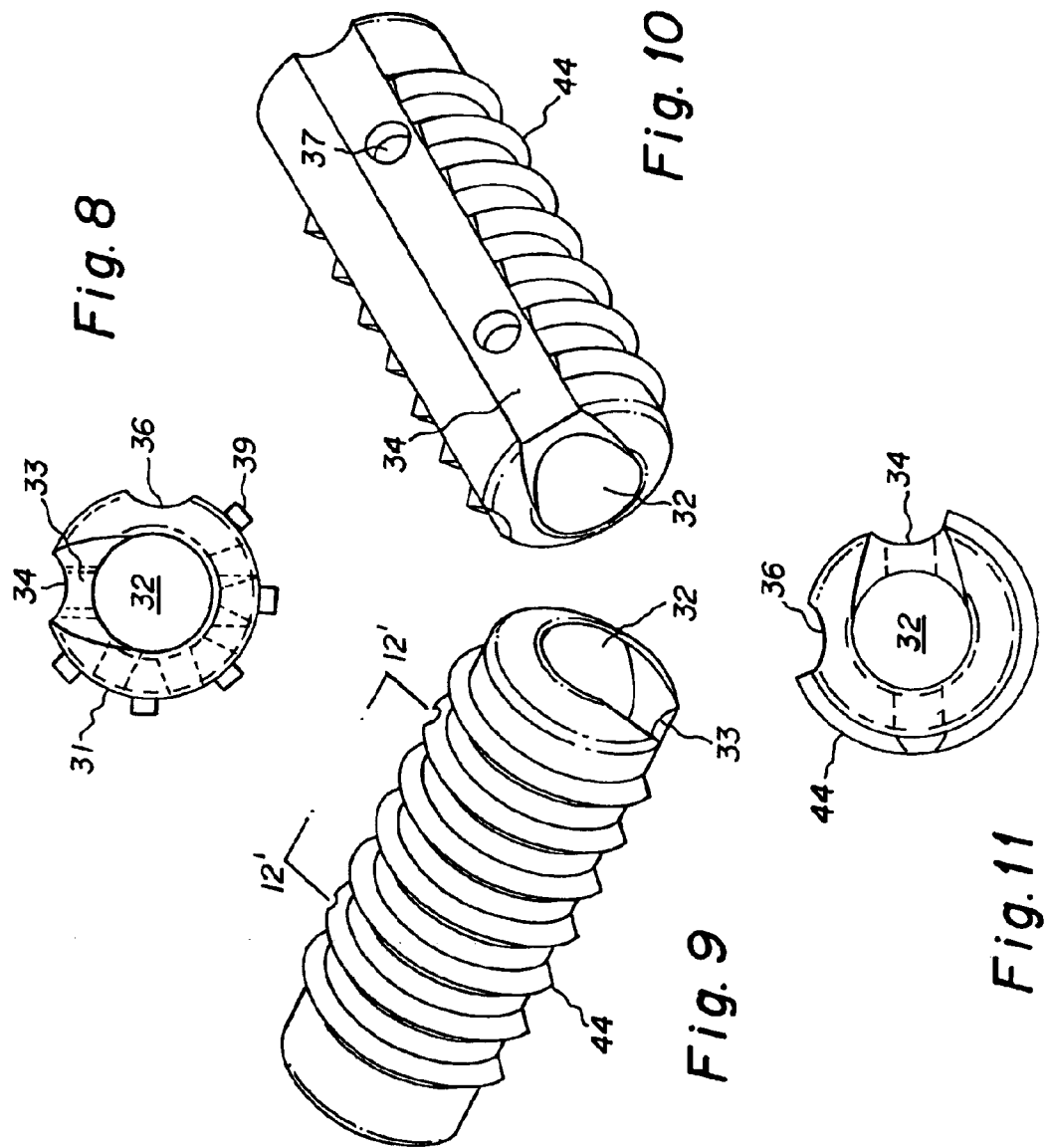

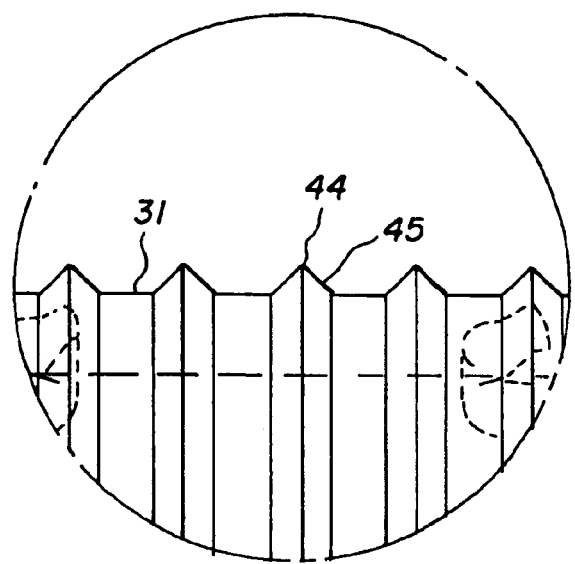
Fig. 12
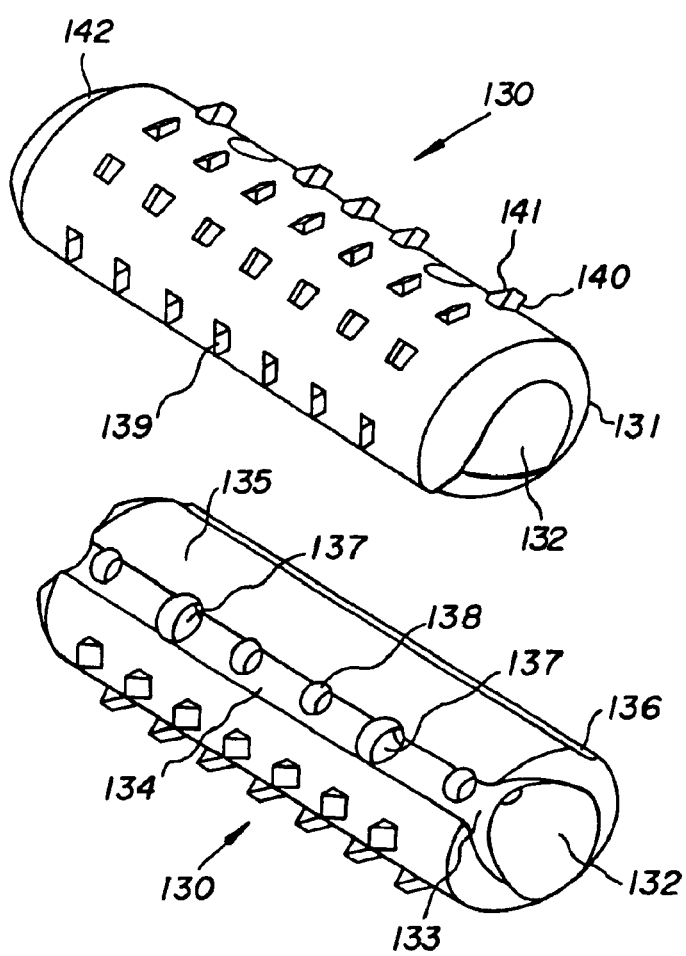
Fig. 13
Fig. 14

BONE-TENDON-BONE ASSEMBLY WITH ALLOGRAFT BONE BLOCK AND METHOD FOR INSERTING SAME

RELATED APPLICATION

There are no related applications.

FIELD OF INVENTION

The present invention is generally directed toward a surgical implant product and more specifically is a shaped allograft bone-tendon-bone implant assembly.

BACKGROUND OF THE INVENTION

Failed ligaments, such as the anterior or posterior cruciate ligaments in the knee joint, significantly limit physical activity and potentially cause chronic knee problems. The anterior cruciate ligament (hereinafter ACL) and the posterior cruciate ligament (PCL) to a lesser extent are often torn during sports related injuries or as result of traumatic stresses. Ligament reconstruction with allograft and autograft tissue has been shown to improve joint function and provide long term improvement in restoration of physical activity. A common surgical method of repair of an ACL is harvesting a patients patellar tendon with bone blocks from the tibia and patella. The bone-patellar tendon-bone implant offers several advantages, including the high initial tensile strength, stiffness, proper length, rigid fixation and direct bone-to-bone incorporation.

The anterior cruciate ligament of the knee functions to resist anterior displacement of the tibia from the femur at all flexion positions. The ACL also resists hyperextension and contributes to rotational stability of the fully extended knee during internal and external tibial rotation. The ACL may also play a role in proprioception. Structurally, the ACL attaches to a depression in the front of the intercondylar eminence of the tibia extending postero-superiorly to the medial wall of the lateral femoral condyle.

Partial or complete tears of the ACL are very common, comprising about 100,000 outpatient procedures in the U.S. each year. The preferred treatment of the torn ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons of the patient are used for the reconstruction; placement of intraarticular hardware is required for ligament fixation; and anterior knee pain frequently occurs. Moreover, recent reviews of cruciate ligament reconstruction indicate an increased risk of degenerative arthritis with intraarticular ACL reconstruction in large groups of patients.

A second method of treating ACL injuries, referred to as "primary repair", involves suturing the torn structure back into place. Primary ACL repair has the potential advantages of a limited arthroscopic approach, minimal disruption of normal anatomy, and an out-patient procedure under a local anesthetic. The potential disadvantage of primary cruciate ligament repair is the perception that over the long term, ACL repairs do not provide stability in a sufficient number of patients, and that subsequent reconstruction may be required at a later date. The success rate of such anterior cruciate ligament repair has generally hovered in the 60% to 70% range.

The autogenous patellar tendon is an excellent tendon replacement source, providing proper tendon length and bone blocks that are fully osteointegrated without immunological rejection. Unfortunately harvesting autogenous bone-tendon-bone (hereinafter B-T-B) also has a number of adverse effects, including donor morbidity (pain), patellar fracture, tendon rupture and degeneration of the patellofemoral articular surface. As an alternate to autogenous graft tissue, synthetic materials have previously received FDA approval. In this regard polyester braids, steel wire and PTFE (GORE-TEX) have been used surgically. All of these materials have failed to integrate into the bone resulting in the tendon's inability to sustain the tensile and torsional loads applied to the knee in normal usage. Nearly all of these synthetic repairs have been revised with autogenous and/or allograft tissue.

There is a limited supply of allograft bone-patellar tendon-bone (B-PT-B) tissue due in large part to the number of donors that qualify according to the selective donor acceptance criteria. As a result of the limited number of available grafts there is a large demand for such grafts. Accordingly a cortical bone block geometry has been developed to provide bone block fixation for an allograft or autograft tendon B-T-B graft with performance characteristics that meet or exceed conventional B-T-B loads.

The use of substitute bone tissue dates back around 1800. Since that time research efforts have been undertaken toward the use of materials which are close to bone in composition to facilitate integration of bone grafts. Development have taken place in the use of grafts of a mineral nature such as corals, hydroxyapatites, ceramics or synthetic materials such as biodegradable polymer materials. Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Human allograft tissue is widely used in orthopaedic, neuro-, maxillofacial, podiatric and dental surgery. The tissue is valuable because it is strong, biointegrates in time with the recipient patient's tissue and can be shaped either by the surgeon to fit the specific surgical defect or shaped commercially in a manufacturing environment. Contrasted to most synthetic absorbable or nonabsorbable polymers or metals, allograft tissue is biocompatible and integrates with the surrounding tissues. Allograft bone occurs in two basic forms; cancellous and cortical. Cortical bone is a highly dense structure comprised of triple helix strands of collagen fiber, reinforced with hydroxyapatite. The cortical bone is a compound structure and is the load bearing component of bones in the human body. The hydroxyapatite component is responsible for the high compressive strength of the bone while the collagen fiber component contributes in part to torsional and tensile strength.

Many devices of varying shapes and forms can be fabricated from allograft cortical tissue by machining. Surgical implants such as pins, rods, screws, anchors, plates, intervertebral spacers and the like have been made and used successfully in human surgery. These pre-engineered shapes are used by the surgeon in surgery to restore defects in bone to the bone's original anatomical shape.

Allograft bone is a logical substitute for autologous bone. It is readily available and precludes the surgical complications and patient morbidity associated with obtaining autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

The combination of natural cortical bone with very desirable mechanical strength and the addition of synthetic (recombinant) BMPs provides a superior form of tissue for surgical use retaining all of the mechanical properties of the cortical component and the accelerated healing offered by the BMPs.

U.S. Pat. No. 5,972,368 issued on Oct. 26, 1999 discloses the use of cortical constructs (e.g. a cortical dowel for spinal fusion) which are cleaned to remove all of the cellular material, fat, free collagen and non-collagenous protein leaving structural or bound collagen which is associated with bone mineral to form the trabecular struts of bone. It is stated that the natural crystalline structure of bone is maintained without the risk of disease transmission or significant immunogenicity. Thus the shaped bone is processed to remove associated non-collagenous bone proteins while maintaining native bound collagen materials and naturally associated bone minerals. The surface of a machined cortical bone surface is characterized by a wide variety of openings resulting from exposure by the machining process of the Haversian canals present throughout cortical bone. These canals serve to transport fluids throughout the bone to facilitate the biochemical processes occurring within the bone. They occur at variable angles and depths within the bone.

In French Patent Applications Numbers 2,582,517 and 2,582,518 treatment of fragments of bones taken from animals, primarily cattle were partially demineralized and tanned with glutaraldehyde. The bone elements to be implanted are cut to the desired shape from an ox bone which has been subjected to a treatment comprising a degreasing step with an organic solvent such as ethanol, a demineralization step with a calcium extraction agent such as hydrochloric acid and tanning with glutaraldehyde and subsequent washings. Similar demineralization of bone is shown in U.S. Pat. No. 5,585,116 issued Dec. 17, 1996. This patent also notes that it is known that partial demineralization facilitates integration of a bone graft. This is accordingly followed by different complementary steps which are intended either to deproteinize the bone completely or to act on the nature of the proteins which then remain linked within the bone matrix or else to increase this proportion of proteins.

Much of the structure and many of the properties of original tissues may be retained in transplants through use of xenogeneic or heterograft materials, that is, tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel heterografts are disclosed in WO 84/03036. However, none of these disclosures describe the use of a xenograft for ACL replacement.

Xenograft materials must be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional cross linking through the side chain carboxyl groups of aspartic and glutamic acid residues of the collagen polypeptide. Glutaraldehyde and diamine tanning also increases the stability of the xenograft tissue.

U.S. Pat. No. 5,562,669 issued Oct. 8, 1996 discloses a B-T-B tendon anchor device using autologus bone plugs taken from the cores drilled out from the bone tunnels of the patient or alternatively donor bone, namely allograft bone to make the bone plugs. The linear cylindrical plug member is provided with two longitudinal substantially parallel grooves cut on opposite sides of each bone plug which provide a recess in which the tendon can be seated. A notch may also be drilled if desired across one end of the bone plug so that the tendon can be wrapped alongside and around the end of the bone plug without protruding excessively from the plug. Suture holes can be cut through the bone plug for attaching the tendon to the plug as is shown in FIGS. 4a and 4b. The perfectly symmetric pattern of the '669 presents the tendon equally on both sides of the bone block.

Likewise U.S. Pat. No. 5,632,748 issued May 27, 1997 discloses a B-T-B tendon anchor device formed of plastic, bone, stainless steel or any other suitable material. The body is tapered and formed with a groove to receive a fixation screw and two curved recesses to hold a tendon which is looped over the device. The fixation groove is provided with threads (FIG. 3) and the tendon grooves are provided with teeth. (FIG. 4). A two piece version having a tongue and groove and stepped mating faces for joinder with two tendon grooves is shown in FIG. 7.

U.S. Pat. No. 6,264,694 issued Jul. 24, 2001 discloses a spherical member having a through going bore and parallel recessed surfaces which enable it to be tied to the end of a soft tissue ligament graft to allow the graft to be secured within the bone tunnel by an interference screw.

SUMMARY OF THE INVENTION

The present invention in various embodiments is directed to a bone-tendon-bone composite graft for use in tendon and cruciate ligament reconstruction. The process of the present invention is directed to ligament or tendon reconstruction surgery. In the inventive surgical installation, a bone tunnel is drilled in each of two bones of the joint. In knee surgery, these are the femur and the tibia although other joints held in place by tendons could be substituted. The allograft bone blocks are pre-machined to form a cylindrical central through going bore and two longitudinal substantially parallel channels which are parallel to the axis of the central bore and are formed longitudinally along the outer surface of the bone block. A rounded recess is cut in the end of the bone block leading from the central bore to one of the channels. At least one tendon replacement member, such as a semitendinous, patellar or gracilis tendon or a combination of tendons is extended between the bone blocks through the central bore of each bone block and over an end connector recess pathway and back along a parallel channel formed on the outer surface of each bone block. The tendon replacement is in turn attached to the two bone blocks. Each bone block is inserted into one of the bone tunnels and secured therein by an interference screw which inserted into the other channel formed on the outside surface of the bone block. The use of the bone-tendon-bone composite graft of the invention results in a reconstructed tendon.

The bone block for modular tendon assembly is directed toward a B-T-B graft for use in orthopedic surgical procedures. The substantially cylindrical bone block invention is provided with parallel channels cut in the outer surface of the bone block to receive and hold a tendon and to accommodate a fixation screw. An end channel or guide way is cut into a curved or tapered end of the bone block and leads from a channel into the central bore to provide a pathway for the tendon loop. A radial through going suture bore is cut transversely to the axis of the channels and at least a portion of the exterior surface of the block opposite the screw fixation groove is provided with a plurality of outwardly extending teeth forming a toothed pattern or a radial rib pattern. The present invention overcomes the current problem of over sizing the outside diameter of the tendon-block construct which cannot be overcome by making the tendon slot deeper so as to cause the tendon to ride deeper in the block. This slot deepening would weaken the bone block by reduction of its effective cross-section so that the bone block might be crushed by the placement of the interference screw and the pressure created on the bone block.

It is thus an object of the invention to provide a shaped bone implant construct having a fully mineralized bone block or a partially demineralized cortical bone layer with an interior mineralized bone section to provide compression strength to the implant bone construct.

It is another object of the invention to utilize a partially demineralized shaped bone implant structure to approximate the mechanical strength characteristics of a natural bone-tendon-bone to provide overall strength and initial durability to the structure.

It is also an object of the invention to provide a pre-machined bone derived structure which can effectively promote new bone growth and accelerate healing.

It is an additional object of the invention to construct a bone block of the inventive design to provide a significantly thinner bone block cross-sectional diameter.

It is yet another object of the invention to create a bone-tendon-bone assembly which mimics the asymmetrical configuration of natural bone-tendon-bone constructs.

It is also an object of the invention to create a bone-tendon-bone assembly which can be easily handled by the physician during surgery which eliminates or significantly reduces the physician from carving the respective bone blocks.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 3 is a view of the knee showing the tibia and femur with tunnels cut there through;

FIG. 8 is an end view of the bone block of FIG. 7 taken from end view 8'—8';

FIG. 9 is a perspective view of another embodiment of the inventive bone block with an exterior thread;

FIG. 10 is a perspective view of the bone block of FIG. 9 in a rotated orientation;

FIG. 11 is an end view of the bone block of FIG. 10;

FIG. 12 is an enlarged partial view of a rib section of FIG. 9 taken from section 12'—12';

FIG. 13 is a perspective view of an alternate embodiment of the inventive bone block having an oval cross section;

FIG. 14 is a perspective view of the bone block embodiment of FIG. 13 in a reverse and rotated orientation;

DETAILED DESCRIPTION OF THE INVENTION

The preferred embodiment and best mode of the present invention is shown in FIGS. 4–8.

Figures 1, 2:
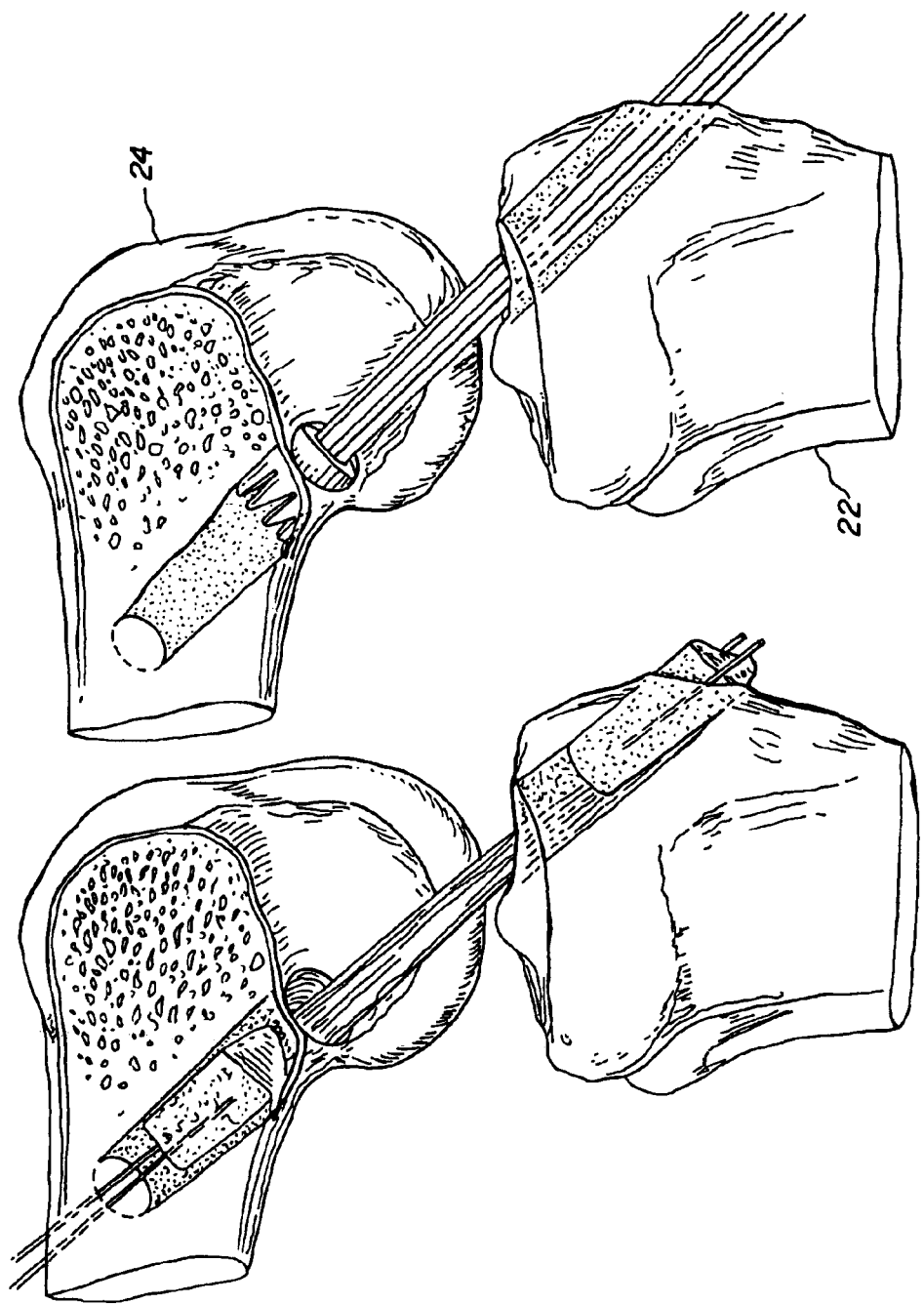
FIG. 1 is a perspective view of a standard prior art bone-tendon-bone implant.
FIG. 2 is a perspective view showing tunnel preparation for the inventive bone-tendon-bone assembly.
Figure 4:
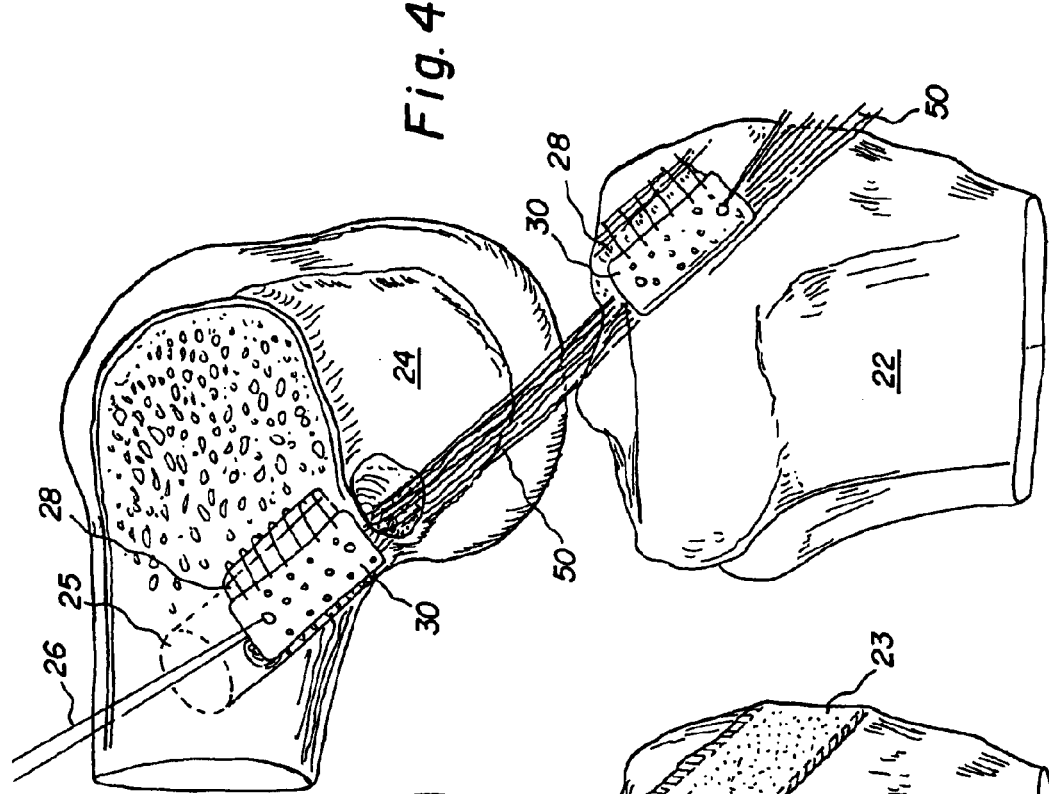
FIG. 4 is a perspective view of the inventive bone-tendon-bone assembly implanted and secured in a knee joint.
Figure 3:
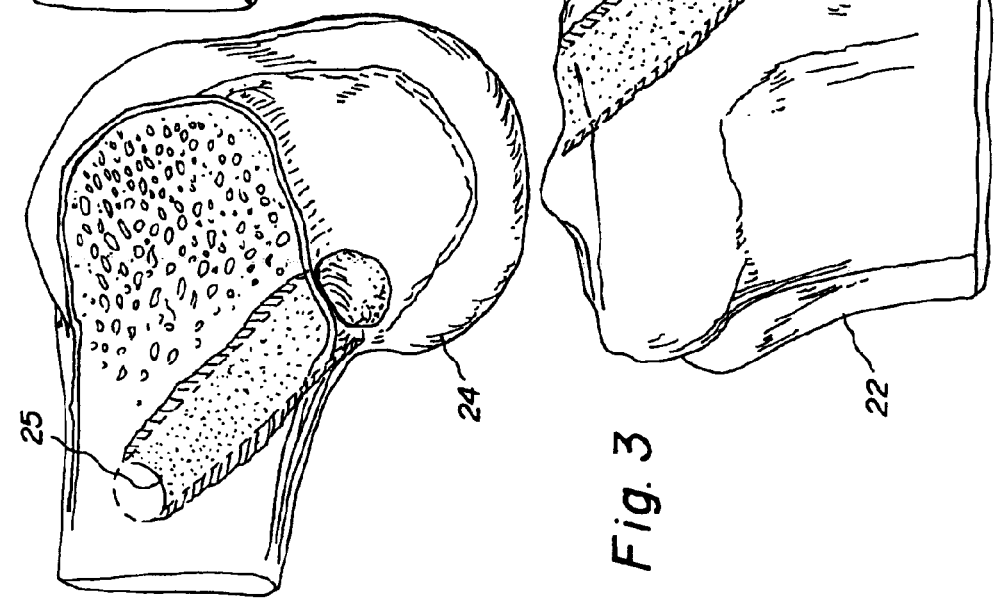

As shown in the drawings, a reconstructed bone-tendon-bone (B-T-B) assembly 10 for a knee joint is shown in FIG. 4 in accordance with the present invention. The cruciate ligament reconstruction surgical operation can be conducted as an open orthopedic surgery, or through arthroscopic surgery. While the description of the invention is primarily directed to knee reconstruction, the present invention can easily be adapted to other joints requiring ligament or tendon replacement.

A number of surgical methods and variation of the same can be used in the knee tendon reconstructive surgery. Representative methods which are exemplary but not exclusive or limited are referred to as the Lipscom et al. Technique, the Puddu Technique, the Zaricznyj Technique, the Zarins and Rower Techniques and are set forth and fully explained in Chapter 29, Knee Injuries, Campell's Orthopaedics (1998, 9$^{th}$ Ed.) and are incorporated herein by reference. In most B-T-B procedures anteromedial and distal lateral bores are drilled to give access to the knee joint for these procedures.

In the standard ACL reconstruction, the intercondylar notch is prepared by drilling the femoral tunnel of the ACL. The tibial hole is prepared by drilling using a cannulated reamer of 8 mm to 12 mm diameter and the intra-articular fluid is drained. The cannulated system is used to place the tunnels anatomically over a guide wire in the tibial and femoral anatomy. The tibial tunnel entrance is midway between the tibial tubercle and the posterior medial edge of the proximal tibia, approximately 3 finger breadths below the joint line. The exit for the tibia tunnel is the posterior medial footprint of the native ACL. With the knee positioned at 90 degrees of flexion, the guide pin is placed in the intercondylar notch and exits the superior lateral femur just above the flare of the condyle. The femoral tunnel is then placed using a cannulated reamer over the guide wire to accommodate a bone block. The graft is passed into position in the femoral tunnel and fixed with an interference screw.

The two major bones that meet at the knee joint are the tibia 22 and the femur 24. Bone tunnels 23 and 25 are drilled through each of these two bones 22, 24 respectively. The tunnels 23 and 25 may be drilled with a regular drill that crushes and removes the bone within the tunnel but it is preferable to use a coring reamer to drill the bone tunnels. The reamer drills out a core of bone through each of the bone tunnels. The knee is flexed or extended a variable amount in order to properly position the femoral tunnel. The reamer is then directed through the tibial tunnel for drilling in and through the femur. The bone core from the femur is removed. Standard deburing and debridement procedures are followed.

Figure 5:
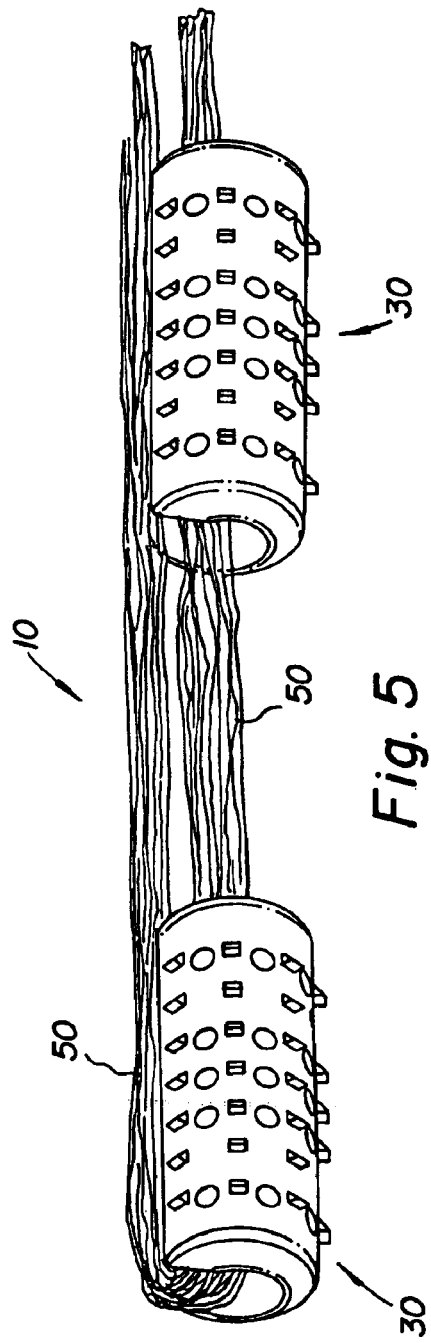
FIG. 5 is an enlarged perspective view of the inventive bone-tendon-bone assembly of FIG. 4 prior to implantation in a knee joint.
Figure 7:
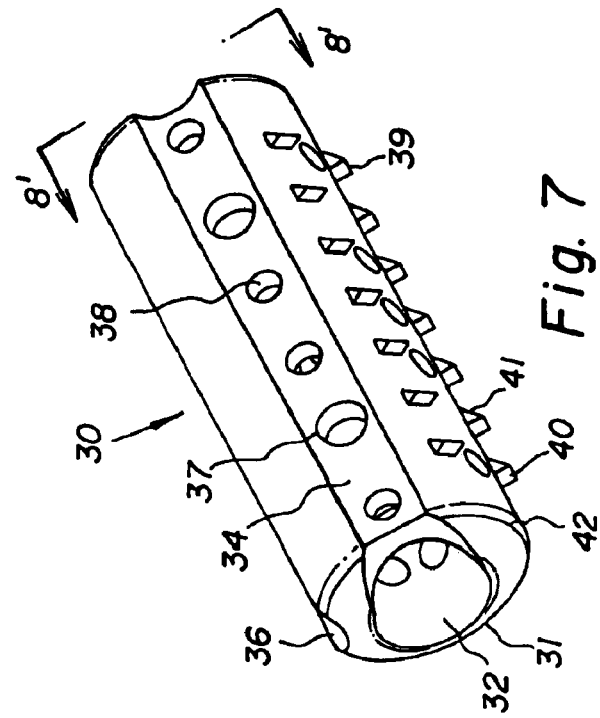
FIG. 7 is a perspective view of the bone block of FIG. 6 in a reverse and rotated orientation.
Figure 6:
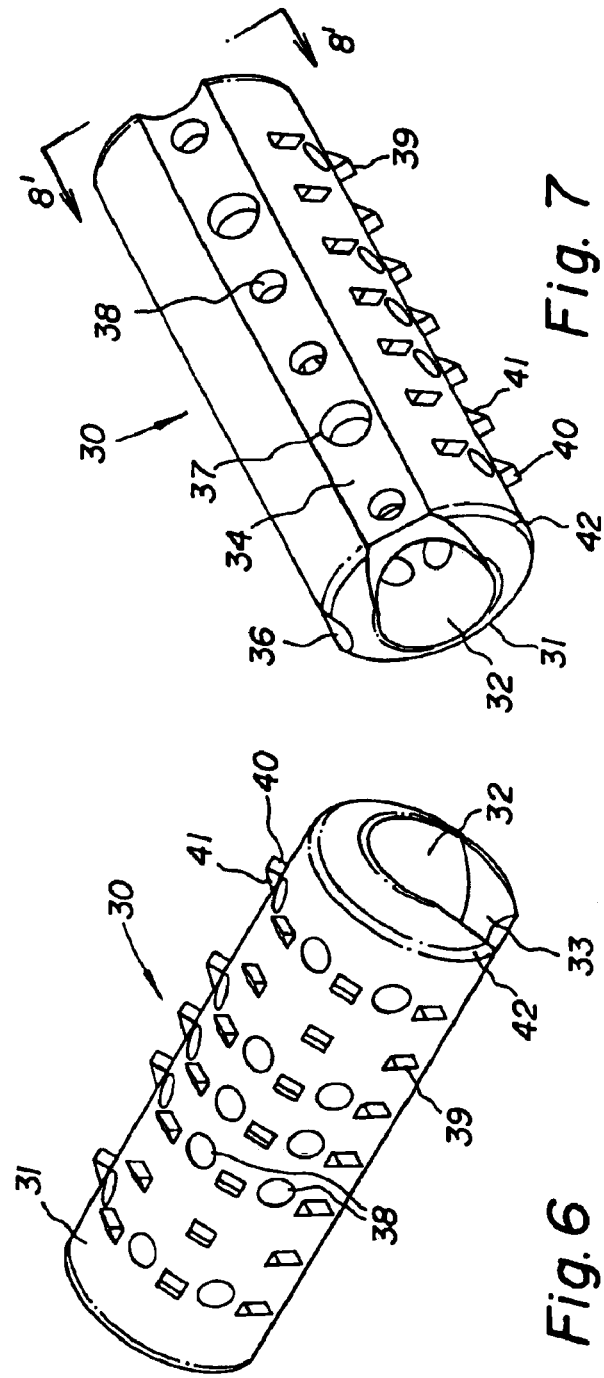
FIG. 6 is a perspective view of the inventive bone block.

After the cores have been drilled out forming the bone tunnels 23 and 25, an allograft B-T-B assembly with pre-machined bone blocks 30 and an attached treated tendon member(s) 50 is inserted into the bone tunnels by pulling the respective bone blocks into the tunnels via sutures 26 as seen in FIG. 4 with the bone blocks being fixed in the tunnel by an interference screw 28 which engages the bone block and the tibia and/or femur to hold the tendon in place. The tendon(s) pass through a block central bore and along an external channel. As can be seen in FIGS. 4–8 a bone block body 30 is cut into a cylindrical shape typically ranging from 8 mm to 12 mm in diameter with a curved outer surface 31 and has a central through going bore 32 cut there through along the anatomical canal and two longitudinal substantially parallel channels 34 and 36 cut into the outer surface 31 of the bone bock to provide a surface for seating the looped tendon 50 and inserting an interference fixation screw 28 to hold the bone block 30 in place in the tunnel. Channels 34 and 36 are preferably cut in the exterior surface of the block so that the midpoint axis of each channel falls at a 45 degree angle taken from a diameter line running through a mid point of the arc between the channels. Thus both channels fall on the same semi-circle of the cylindrical bone block. The bone block diameter can vary from 8–12 mm with a corresponding length of 25–35 mm depending upon surgeon preference. An end recess or pathway 33 is cut into the end of the bone block body 30 forming a recessed pathway leading to the central bore 32 and parallel channel 34 so that the tendon(s) 50 can be looped over a curved surface so that there will be no sharp edges engaging the tendon(s) 50 as is shown in FIG. 5. Suture holes 37 are radially cut through the bone block from the channel 34 into the central bore 32 for attaching the tendon(s) 50 to the bone block 30. The suture holes are drilled into the channel 34 radially through the bone block. In the preferred embodiment, at least two (2) such suture holes 37 are drilled through the bone block. The sutures 26 are used to pull the bone block into the desired location in tunnels 23 and 25 and the pre-drilled suture holes in the bone face are located at the bone face at a location so as not to have the suture 26 cut by the interference screw 28. A plurality of circulation holes 38 are cut radially into the surface of the bone block body leading from the outer surface 31 to the central core 32 to expose the interior of the bone block and allow faster bone growth. These holes preferably have a diameter of 1 mm or less. A plurality of angularly shaped teeth 39 are cut into the outer surface 31 in parallel rows equidistantly spaced apart to provide additional gripping of the bone block 30 in the tunnel. The teeth 39 are preferably formed or cut with a vertical face 40 and a sloping angled face 41 cut at a 40 degree angle as is shown in FIG. 6. It is of course within the scope of the invention to stagger the rows of teeth to present multiple variations of same or to apply a thread or ridge on the outside exterior surface. The teeth 39 are located on only one side the bone block body 30 as can be readily seen in FIG. 7. The inner end face 42 of each bone block is cut on an angle or beveled to provide a flush alignment of the bone block with the articulating end of the tunnel at both the tibial and femoral placement. This will minimize the contact between the bone block and the articulating cartilage on the faces of the knee joint. The femoral angle will preferably have a range from 5 to 15 degrees and tibial angle from 15 to 30 degrees.

As can be seen in the rib variation of FIGS. 9–12, the teeth 39 have been replaced with a rib structure. A plurality of ribs 44 are cut into the outer surface 31 equidistantly spaced apart to provide additional gripping of the bone block 30 in the tunnel. The ribs 44 are cut with two 45 degree angled sides 45. While only suture holes 37 are shown, circulation holes can also be cut from the surface to the central bore.

Figure 15:
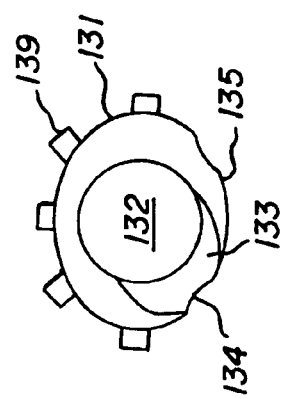
FIG. 15 is an end view of the bone block embodiment of FIG. 13.

As can be seen in FIGS. 13–15 in an alternate embodiment, a bone block body 130 is cut into a longitudinal form with an oval or elliptical cross sectional shape typically ranging from 8 mm to 12 mm in the major diameter axis with a curved outer surface 131 and has a central through going bore 132 cut there through. Two longitudinal substantially parallel channels 134 and 136 are cut into the outer surface 131 of the bone bock to provide a surface for seating the looped tendon(s) 50 and inserting an interference fixation screw 28 to hold the bone block 130 in place in the tunnel. Channels 134 and 136 are preferably cut in the exterior surface of the block 130 so that the midpoint axis of each channel falls at a 45 degree angle taken from a diameter line running through a mid point of an arc between the channels. Thus both channels fall on the same side of the bone block. The bone block can vary from 8–12 mm at its major diameter with a corresponding length of 25–35 mm depending upon surgeon preference. An end guide path or pathway 133 is cut into the end of the bone block body 130 forming a recessed pathway leading to the central bore 132 and parallel channel 134 with the tendon(s) 50 being looped over a curved surface so that there will be no sharp edges engaging the tendon(s) 50. Suture holes 137 are radially cut through the bone block from the channel 134 into the central bore 132 for attaching the tendon(s) 50 to the bone block 130. The suture holes are drilled into the channel 134 radially through the bone block. In the preferred embodiment, at least two (2) such suture holes 137 are drilled through the bone block. Sutures 26 are used to pull the bone block 130 into the desired location in tunnels 23 and 25 and the pre-drilled suture holes in the bone face are located at the bone face at a location so as not to have the suture 26 cut by the interference screw 28. A plurality of circulation holes 138 are cut radially into the surface of the bone block body leading from the outer surface 131 to the central core 132 to expose the interior of the bone block bone and allow faster bone growth. A plurality of shaped teeth 139 are cut into the outer surface 131 in parallel rows equidistantly spaced apart to provide additional gripping of the bone block 130 in the tunnel. The teeth 139 are preferably formed or cut with a vertical face 140 and a sloping angled face 141 cut at a 40 degree angle. It is of course within the scope of the invention to stagger the rows of teeth to present multiple variations of same or to apply a thread or ridge on the outside exterior surface. The teeth 139 are located on only one side the bone block body 130 as can be readily seen in FIG. 13 with the other side presenting a smooth surface 135. The inner end face 142 of each bone block is cut on an angle or bevel to provide a flush alignment of the bone block with the articulating end of the tunnel at both the tibial and femoral placement. This will minimize the contact between the bone block and the articulating cartilage on the faces of the knee joint. The femoral angle will preferably have a range from 5 to 15 degrees and tibial angle from 15 to 30 degrees.

Figure 16:
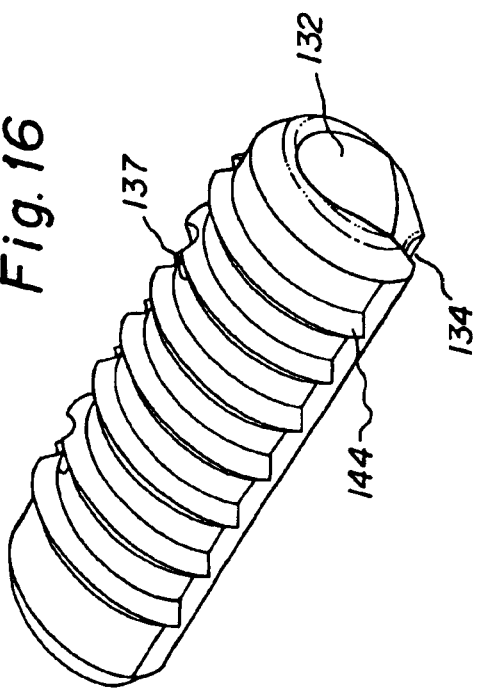
FIG. 16 is a perspective view of the alternate embodiment of the inventive bone block with an exterior thread.
Figure 18:
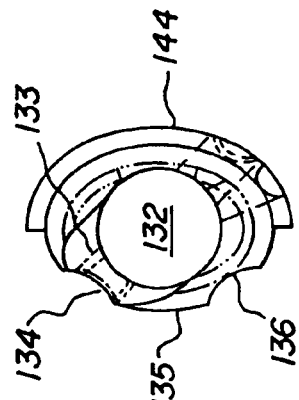
FIG. 18 is an end view of the bone block embodiment of FIG. 17.
Figure 17:
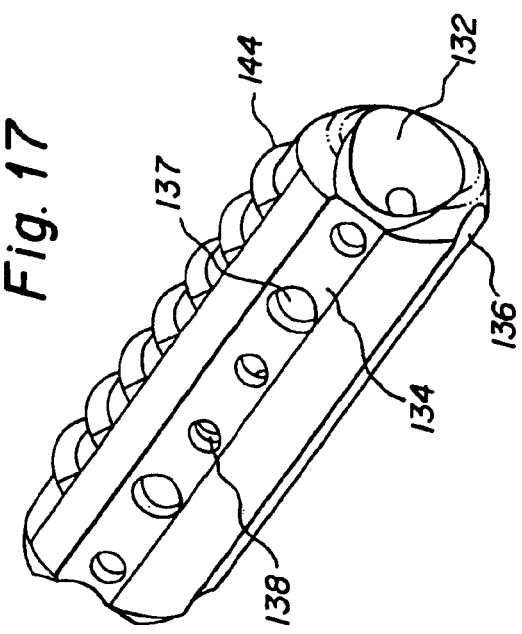
FIG. 17 is a perspective view of the bone block embodiment of FIG. 16 in a reverse and rotated orientation.

As can be seen in FIGS. 16–18 the teeth 139 have been replaced with a rib structure. A plurality of ribs 144 are cut into the outer surface 131 equidistantly spaced apart to provide additional gripping of the bone block 130 in the tunnel. The ribs 144 are cut with two 45 degree angled sides.

The asymmetry of the inventive design also provides a significantly thinner bone block cross-sectional diameter, This is critical during the entry and proper placing of the bone block in the tunned drilled by the surgeon. Thus the tendon is placed in an asymmetric orientation relative to the bone block. This is very much like the symmetry in the patellar bone-tendon-bone (either autologous or allogenic). The success of the patellar BTB in providing satisfactory load bearing and eventual healing in the ACL application may be in part due to the asymmetry.

When using multiple strands of tendons 50, as an example, a semitendinosus tendon and/or gracilis tendon are extended between both of the bone blocks 30, 130. The tendon(s) 50 are preferably sutured to themselves to form a double loop as shown in FIGS. 4 and 5. Sutures 26 are also used through the suture holes 137 to attach the tendon(s) to each of the bone blocks. The ligament replacement of an embodiment of the invention may include one or more of the following tendons: patellar, semitendinosus, gracilis, quadriceps, adductor magnus, the hamstrings, peroneus longus and hallucis longus. The tendons typically run from 180 mm to 200 mm in length and when harvested are fresh frozen or freeze dried after cleaning for preservation for use in the B-T-B assembly. The tendon can be sterilized with radiation dosages as is well known in the art. As such the tendon structure or member combining one or more of the above noted tendons will connect the two bone blocks. Single bone blocks can be used with the achilles, biceps femoris and quadriceps tendons as these come naturally with a bone block.

Still further embodiments of the invention may substitute or combine man made or artificial fibers or human tissue for the tendons for use as the ligament replacement. After the bone blocks have been inserted in the bone tunnels, the sutures 26 hanging from one end of the composite graft are attached to a needle, a passer or other conventional graft placement tool.

The proper tension is then applied to the graft by pulling on the suture 26 hanging out from the tibial incision. A driver and a headless interference screw are then inserted through the tibial incision for driving the screw along the channel 36, 136 of the bone block. In affixing the composite graft 10 within a bone tunnel, contact between an interference screw 28 and the tendon 50 should be avoided so as not to cut or tear the tendon. To better insure that the screw is out of contact with the tendon, the interference screw 28 should be driven along the bone portion of the bone block channel 36, 136 and the respective bone tunnel wall. The sutures 26 are then cut and the incisions are closed.

While this operation has been discussed in terms of using allograft bone blocks, alternative sources of bone blocks may be substituted such as xenograft bone or synthetic graft materials. With any of these alternatives, the bone blocks may be shaped as described above for the graft.

The unique features of bone that make it desirable as a surgical material are, its ability to slowly resorb and be integrated into the space it occupies while allowing the bodies own healing mechanism to restore the repairing bone to its natural shape and function by a mechanism known in the art as creeping substitution. The second feature is the high mechanical strength arising from the collagen fiber reinforced hydroxyapatite compound structure. The creeping substitution mechanism, takes considerable time and some forms of cortical bone in their natural, unmodified biological state have been found to persist for over one year before completely remodeling. Thus a means of accelerating the rate of biointegration of cortical bone would improve the rate of healing and benefit the recipient patient.

The cylindrical cortical bone block 30, 130 can have its surface 31, 131 and or central cavity 32, 132 modified by acid treatment to remove a layer of the inorganic mineral. Thus the surface of cortical bone constructs can be modified by acid treatment to remove a layer of the inorganic, mineral material in such a way as to leave the mechanical properties substantially unchanged or to provide a construct having suitable compression and bending strength. This allows the addition of BMP's and other desirable additives which are more fully set forth on pages 15 and 16 to be introduced to the surface and thereby enhance the healing rate of the cortical bone in surgical procedures. The process also exposes the naturally occurring BMP's near the surface and renders the surface with biological properties similar to fully demineralized bone (DMB). The inner mass of the bone construct would be left intact to contain the naturally occurring BMP's.

It is well known that bone contains osteoinductive elements known as bone morphogenetic proteins (BMP). These BMP's are present within the compound structure of cortical bone and are present at a very low concentrations, e.g. 0.003%. BMP directs the differentiation of pluripotential mesenchymal cells into osteoprogenitor cells which form osteoblasts. The ability of freeze dried demineralized cortical bone to facilitate this bone induction principle using BMP present in the bone is well known in the art. However, the amount of BMP varies in the bone depending on the age of the bone donor and the bone processing. Based upon the work of Marshall Urist as shown in U.S. Pat. No. 4,294,753, issued Oct. 13, 1981 the proper demineralization of cortical bone will expose the BMP and present these osteoinductive factors to the surface of the demineralized material rendering it significantly more osteoinductive. The removal of the bone mineral leaves exposed portions of collagen fibers allowing the addition of BMP's and other desirable additives to be introduced to the demineralized outer treated surface of the bone structure and thereby enhances the healing rate of the cortical bone in surgical procedures. The treatment process also exposes the naturally occurring BMP's at the surface and renders the surface with biological properties similar to full demineralized bone (DBM). The inner mass of the bone mineral of the shaped bone block construct would be left intact to contain the naturally occurring BMP's and trace elements as noted above.

The bone blocks of the present invention were prepared by machining fibula although femoral, femoral or tibia cortical bone and bone taken from the humerus, ulna or radius can be used.

It is also possible to add one or more rhBMP's to the surface of the treated bone shape by soaking and being able to use a significantly lower concentration of the rare and expensive recombinant human BMP to achieve the same acceleration of biointegration. The addition of other useful treatment agents such as vitamins, hormones, antibiotics, antiviral and other therapeutic agents could also be added to the surface modified layer.

Any number of medically useful substances can be incorporated in the bone block and tendon assembly by adding the substances to the assembly. Such substances include collagen and insoluble collagen derivatives, hydroxyapatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicilin, azactam, tobramycin, clindamycin, gentamycin and silver salts. It is also envisioned that amino acids, peptides, vitamins, co-factors for protein synthesis; hormones; endocrine tissue or tissue fragments; synthesizers; enzymes such as collagenase, peptidases, oxidases; polymer cellpl scaffolds with parenchymal cells; angiogenic drugs and polymeric carriers containing such drugs; collagen lattices; biocompatible surface active agents, antigenic agents; cytoskeletal agents; cartilage fragments, living cells such as chondrocytes, bone marrow cells, mesenchymal stem cells, natural extracts, tissue transplants, bioadhesives, transforming growth factor (TGF-beta), insulin-like growth factor (IGF-1), platelet derived growth factor, fibroblast GF, osteopontin VEGF, blood elements; growth hormones such as somatotropin; bone digestors; antitumor agents; fibronectin; cellular attractants and attachment agents; immunosuppressants; permeation enhancers, e.g. fatty acid esters such as laureate, myristate and stearate monoesters of polyethylene glycol, enamine derivatives, alpha-keto aldehydes can be added to the composition.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A sterile composite graft comprising: first and second bone blocks, each bone block defining a central through going bore having a cross section which will allow a ligament replacement to be passed there through and at least one longitudinal channel cut substantially parallel to the axis of the central through going bore in the exterior surface of said bone block and a ligament replacement mounted to said bone blocks, said ligament replacement extending through said central bore of said bone blocks and around said first and second bone blocks seated in said longitudinal channel.

2. A sterile composite graft as claimed in claim 1 wherein said ligament replacement comprises at least one tendon taken from a group of tendons consisting of a semitendinous tendon, a patellar tendon, gracilis tendon, quadriceps tendon, adductor magnus tendon, peroneus tendons, tibialis tendons and hallucis achilles tendon.

3. A sterile composite graft as claimed in claim 1 wherein said first and second bone blocks further define a rounded notch in one end leading from said central bore to a parallel longitudinal channel to accommodate said ligament replacement extending around said bone block from said central bore to a parallel longitudinal channel.

4. A sterile composite graft as claimed in claim 1 wherein said first and second bone blocks further comprise a plurality of holes drilled radially through each of said bone blocks from an outer surface through to the central bore.

5. A sterile composite graft as claimed in claim 1 wherein said first and second bone blocks are constructed of allograft cortical bone.

6. A sterile composite graft as claimed in claim 1 wherein said first and second bone blocks are constructed of xenograft cortical bone.

7. A sterile composite graft as claimed in claim 1 wherein said first and second bone blocks are constructed of ceramic.

8. A sterile composite graft as claimed in claim 1 wherein said first and second bone blocks are constructed of bioabsorbable polymers.

9. A sterile composite graft as claimed in claim 1 wherein said first and second bone blocks define a plurality of radial ribs which extend outward from an outer surface of said bone block.

10. A sterile composite graft as claimed in claim 1 wherein said first and second bone blocks have a second fixation screw channel cut in their outer surface.

11. A sterile composite graft as claimed in claim 1 wherein said first and second bone blocks are oval in shape and define a plurality of holes leading from an outside surface of said bone block to said central through going bore.

12. A sterile composite graft as claimed in claim 11 wherein the angle for a bone block to be placed in a tibial tunnel ranges from about 5 degrees to about 15 degrees.

13. A sterile composite graft as claimed in claim 11 wherein the angle for a bone block to be placed in a femoral tunnel ranges from about 15 degrees to about 30 degrees.

14. A sterile composite graft as claimed claim 11 wherein each bone block includes an additive taken from a group of additives consisting of living cells such as chondrocytes, bone marrow cells, mesenchymal stem cells, natural extracts, tissue transplants, bioadhesives, transforming growth factor (TGF-beta), insulin-like growth factor (IGF-1), platelet derived growth factor, fibroblast GF, osteopontin VEGF, blood elements.

15. A sterile composite graft as claimed in claim 1 wherein said ligament replacement comprises a semitendinosus tendon.

16. A sterile composite graft as claimed in claim 1 wherein said ligament replacement comprises a patellar tendon.

17. A sterile composite graft as claimed in claim 1 wherein said ligament replacement comprises a gracilis tendon.

18. A sterile composite graft as claimed in claim 1 wherein an inner face of each bone block is cut on an angle to provide a flush alignment of the bone block.

19. A sterile bone block for use in implants comprising:
an arcuate bone block body having a central through going bore and at least one substantially parallel longitudinal channel cut in an exterior surface of said bone block body, said bone block body has an oval cross section and at least one suture hole is formed radially from an exterior surface of said bone block body through to the central bore, said bone block body defining a rounded recess formed in one end to accommodate a ligament replacement, said recess extending around a bone block end leading from said central bore to at least one substantially parallel longitudinal channel cut in the exterior surface of said bone block body.

20. A sterile bone block as claimed in claim 19 wherein said bone block body has a pathway notch formed in one end to accommodate a ligament replacement, said pathway notch extending around a bone block end leading from said central bore to the substantially parallel longitudinal channel cut in the exterior surface of said bone block body.

21. A sterile bone block as claimed in claim 19 wherein said bone block body has a plurality of radial ribs which extend outward from an outer surface of said bone block body.

22. A sterile bone block as claimed in claim 19 wherein said bone block body has a bone fixation screw channel cut in its outer surface within 90 degrees of said parallel longitudinal channel.

23. A sterile bone block for use in implants comprising:
an allograft bone block body with an oval cross section having a central through going bore and at least one substantially parallel longitudinal channel cut in an exterior surface of said bone block body, said bone block body has a rounded notch formed in one end to accommodate a ligament replacement, said notch extending around a bone block end leading from said central bore to the substantially parallel longitudinal channel cut in the exterior surface of said bone block body, said bone block body further defining a plurality of holes drilled radially through the body of said bone block from an outer surface through to the central bore.

24. A sterile composite graft as claimed claim 23 wherein each bone block includes an additive taken from a group of additives consisting of living cells such as chondrocytes, bone marrow cells, mesenchymal stem cells, natural extracts, tissue transplants, bioadhesives, transforming growth factor (TGF-beta), insulin-like growth factor (IGF-1), platelet derived growth factor, fibroblast GF, osteopontin VEGF, blood elements.

* * * * *